United States Patent [19]

Maier et al.

[11] Patent Number: 4,677,217
[45] Date of Patent: Jun. 30, 1987

[54] PHOSPHOROUS-CONTAINING PHENYLSULFONAMIDES

[75] Inventors: Ludwig Maier, Arlesheim; Willy Meyer, Riehen; Konrad Oertle, Therwil; Achim Roloff, Rheinfelden; Werner Töpfl, Dornach, all of Switzerland

[73] Assignee: Ciba-Geigy Corporation, Ardsley, N.Y.

[21] Appl. No.: 784,274

[22] Filed: Oct. 4, 1985

Related U.S. Application Data

[62] Division of Ser. No. 562,659, Dec. 19, 1983, Pat. No. 4,559,078.

[30] Foreign Application Priority Data

Dec. 27, 1982 [CH] Switzerland ............ 7562/82

[51] Int. Cl.⁴ .................. C07F 9/32; C07F 9/38
[52] U.S. Cl. .................. 558/190; 260/502.5 D; 558/166
[58] Field of Search ............ 260/947, 502.5 D; 558/190, 166, 191

[56] References Cited

U.S. PATENT DOCUMENTS 3,705,920 12/1972 Patchett ............. 260/947

FOREIGN PATENT DOCUMENTS 1044826 11/1958 Fed. Rep. of Germany ...... 558/190

*Primary Examiner*—Anton H. Sutto
*Attorney, Agent, or Firm*—Edward McC. Roberts; Kevin T. Mansfield

[57] ABSTRACT

Phenylsulfonamides of the formula

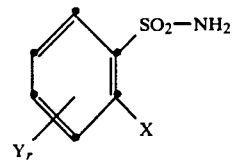

in which X is a group

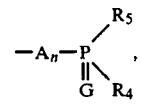

Y is hydrogen, halogen, $C_1$–$C_5$-alkyl, trifluoromethyl, $C_2$–$C_5$-alkenyl, $C_2$–$C_5$-alkynyl, nitro, —COOR$^6$ or —Q—R$^6$, A is oxygen, sulfur, a direct bond, $C_1$–$C_5$-alkylene, $C_2$–$C_5$-alkenylene, $C_1$–$C_5$-halogenoalkylene or —NR$^7$—(CH$_2$)$_m$—; —CH$_2$—NH—(CH$_2$)$_m$; —(CH$_2$)$_m$—NR$^7$— or —O—(CH$_2$)$_p$—, —S—(CH$_2$)$_p$—, —(CH$_2$)$_p$—O— or —(CH$_2$)$_p$—S—, n is zero or one, G is oxygen or sulfur, R$^4$ is $C_1$–$C_5$-alkoxy, $C_1$–$C_5$-halogenoalkoxy, $C_1$–$C_5$-alkylthio, $C_1$–$C_5$-alkyl, $C_1$–$C_5$-halogenoalkyl, phenyl or hydroxyl, R$^5$ is hydrogen, $C_1$–$C_5$-alkoxy, $C_1$–$C_5$-halogenoalkoxy, $C_1$–$C_5$-alkylthio, $C_1$–$C_5$-alkyl or hydroxyl, R$^6$ is hydrogen, $C_1$–$C_5$-alkyl, $C_1$–$C_5$-halogenoalkyl or $C_2$–$C_6$-alkoxyalkyl, Q is oxygen, sulfur, —SO— or —SO$_2$—, R$^7$ is hydrogen, $C_1$–$C_5$-alkyl, phenyl, benzyl or phenyl which is substituted by $C_1$–$C_5$-alkyl, halogen, or nitro, m is a number from zero to three, p is a number from zero to two and r is one or two are useful as intermediates for phosphorous-containing N-phenylsulfonyl-N'-pyrimdinylurea and N-phenylsulfonyl-N'-triazinylurea herbicides.

5 Claims, No Drawings

PHOSPHOROUS-CONTAINING PHENYLSULFONAMIDES

This is a divisional of application Ser. No. 562,659 filed on Dec. 19, 1983, now U.S. Pat. No. 4,559,078.

The present invention relates to novel, herbicidally active and plant growth-regulating, phosphorus-containing N-phenylsulfonyl-N'-pyrimidinylureas and N-phenylsulfonyl-N'-triazinylureas, processes for their preparation, compositions containing them as the active substances, and their use for controlling weeds, in particular selectively in crops of useful plants, or for regulating and inhibiting plant growth.

The phosphorus-containing N-phenylsulfonyl-N'-pyrimidinylureas and N-phenylsulfonyl-N'-triazinylureas according to the invention have the general formula I

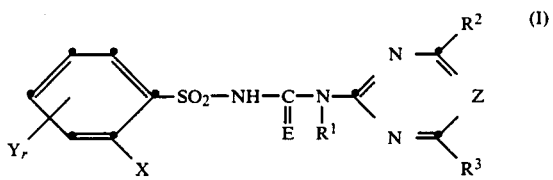

in which X is a group

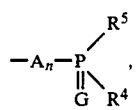

Y is hydrogen, halogen, $C_1$–$C_5$-alkyl, trifluoromethyl, $C_2$–$C_5$-alkenyl, $C_2$–$C_5$-alkynyl, nitro, —$COOR^6$ or —Q—$R^6$, or Q—$R^6$, Z is nitrogen or the methine group, E is oxygen or sulfur, $R^1$ is hydrogen or $C_1$–$C_5$-alkyl and $R^2$ and $R^3$ independently of one another are $C_1$–$C_3$-alkyl, $C_1$–$C_3$alkoxy, $C_1$–$C_3$-halogenoalkyl, $C_1$–$C_3$-halogenoalkoxy, cyclopropyl, amino, methylamino or dimethylamino, and A is oxygen, sulfur, $C_1$–$C_5$-alkylene, $C_2$-alkenylene, $C_1$–$C_5$-halogenoalkylene or —$NR^7$—$(CH_2)_m$—; —$CH_2$—NH—$(CH_2)_m$—; —$(CH_2)_m$—$NR^7$— or —O—$(CH_2)_p$—; —S—$(CH_2)_p$—, —$(CH_2)_p$—O— or —$(CH_2)_p$—S—, n is zero or one, G is oxygen or sulfur, $R^4$ is $C_1$–$C_5$-alkoxy, $C_1$–$C_5$-halogenoalkoxy, $C_1$–$C_5$-alkylthio, $C_1$–$C_5$-alkyl, $C_1$–$C_5$-halogenoalkyl, phenyl or hydroxyl, $R^5$ is hydrogen, $C_1$–$C_5$-alkoxy, $C_1$–$C_5$-halogenoalkoxy, $C_1$–$C_5$-alkylthio, $C_1$–$C_5$-alkyl or hydroxyl, $R^6$ is $C_1$–$C_5$-alkyl, $C_1$–$C_5$-halogenoalkyl or $C_2$–$C_6$-alkoxyalkyl, Q is oxygen, sulfur, —SO— or —$SO_2$—, $R^7$ is hydrogen, $C_1$–$C_5$-alkyl, phenyl, benzyl or phenyl which is substituted by $C_1$–$C_5$-alkyl, halogen or nitro, m is a number from zero to three, p is a number from zero to two and r is one or two.

The invention embraces not only the compounds of the formula I, but also the salts thereof.

Herbicides and plant growth-regulating active substances belonging to the class of sulfonylurea compounds have been known for some time. Active substances of this type are described, for example, in U.S. Pat. No. 4,127,405 or in European Patent Applications Nos. 44,807, 44,808 and 44,809.

In the definitions, alkyl is to be understood as meaning linear or branched alkyl: for example, methyl, ethyl, n-propyl, i-propyl, the four isomeric butyls, n-amyl, i-amyl, 2-amyl, 3-amyl, n-hexyl or i-hexyl.

Alkoxy is to be understood as meaning: methoxy, ethoxy, n-propoxy, i-propoxy and the four isomeric butoxy radicals, but particularly methoxy, ethoxy or i-propoxy.

Examples of alkylthio are methylthio, ethylthio, n-propylthio, i-propylthio and n-butylthio, but particularly methylthio and ethylthio.

Examples of alkenyl radicals are vinyl, allyl, isopropenyl, 1-propenyl, 1-butenyl, 2-butenyl, 3-butenyl, 1-isobutenyl, 2-isobutenyl, 1-pentenyl, 2-pentenyl, 3-pentenyl and 4-pentenyl, but particularly vinyl, allyl and 4-pentenyl.

Examples of alkylsulfinyl are methylsulfinyl, ethylsulfinyl, n-propylsulfinyl and n-butylsulfinyl, but particularly methylsulfinyl and ethylsulfinyl.

Examples of alkylsulfonyl are methylsulfonyl, ethylsulfonyl, n-propylsulfonyl and n-butylsulfonyl, but particularly methylsulfonyl and ethylsulfonyl.

In the definitions, and also in halogenoalkyl, halogenoalkoxy, halogenoalkylsulfinyl, halogenoalkylsulfonyl and halogenoalkylthio, halogen is to be understood as meaning fluorine, chlorine and bromine, but preferably fluorine and chlorine.

Correspondingly, halogenoalkyl or halogenoalkyl moieties of substituents defined above are to be understood as meaning, for example: chloromethyl, fluoromethyl, difluoromethyl, trifluoromethyl, 2-chloroethyl, 2,2,2-trifluoroethyl, 1,1,2,2-tetrafluoroethyl, pentafluoroethyl, 1,1,2-trifluoro-2-chloroethyl, 2,2,2-trifluoro-1,1-dichloroethyl, pentachloroethyl, 3,3,3-trifluoropropyl, 2,3-dichloropropyl and 1,1,2,3,3,3-hexafluoropropyl, but particularly fluoromethyl, chloromethyl, difluoromethyl and trifluoromethyl.

Alkynyl radicals in the definitions of the above symbols are, as a rule, propargyl, 2-butynyl, 3-butynyl and isomeric pentynyl or hexynyl radicals, but the alkynyl radical is preferably represented by propargyl or 2-butynyl or 3-butynyl.

The definition of the group X includes both radicals in which the phosphorus atom is directly attached to the phenyl nucleus, and also those in which there is an oxygen, sulfur, alkylene or alkenylene bridge between the phenyl nucleus and the phosphorus atom, it being also possible for the alkylene bridges to contain further members consisting of hetero-atoms. Preferred radicals X are those in which the phosphorus atom is attached to the phenyl nucleus either directly or via a $C_2$–$C_3$-alkylene or $C_2$–$C_3$-alkenylene bridge. The functional phosphorus group can be present here in various stages of oxidation corresponding to the following parent phosphorus acids: phosphorous acid, phosphoric acid, phosphonous acid, phosphonic acid, phosphinous acid and phosphinic acid. However, the radicals $R^4$ and $R^5$ are preferably $C_1$–$C_5$ alkyl or $C_1$–$C_5$-alkoxy.

The invention also embraces the salts which can be formed by the compounds of the formula I with amines, alkali or alkaline earth metal bases or quaternary ammonium bases.

Mobile protons which can be detached readily from the molecule of the formula I for the formation of salts, are to be found in the phosphorus acid group of the radical X, provided that free hydroxyl groups are present, or on the bridging nitrogen atom between the sulfonyl and carbonyl groups.

Amongst alkali and alkaline earth metal hydroxides, the hydroxides of lithium, sodium, potassium, magnesium or calcium, but particularly those of sodium or potassium, should be singled out as salt-formers.

Examples of amines suitable for the formation of salts are primary, secondary and tertiary aliphatic and aromatic amines, such as methylamine, ethylamine, propylamine, i-propylamine, the four isomeric butylamines, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and i-quinoline, but particularly ethylamine, propylamine, diethylamine or triethylamine and especially isopropylamine and diethanolamine.

Examples of quaternary ammonium bases are, in general, the cations of ammonium halide salts, for example the tetramethylammonium cation, the trimethylbenzylammonium cation, the triethylbenzylammonium cation, the tetraethylammonium cation and the trimethylethylammonium cation, but also the ammonium cation.

Amongst the compounds, according to the invention, of the formula I, preferred compounds are those in which either (a) the bridge $A_n$ is a direct bond, $C_2$–$C_3$-alkylene or $C_2$–$C_3$-alkenylene, or (b) E is oxygen, or (c) $R^1$ is hydrogen, or (d) the radicals $R^2$ and $R^3$ are methyl or methoxy, or (e) G is oxygen, or (f) Y is hydrogen.

Subgroups of compounds which are preferred to a further extent are those wherein the bridge $A_n$ is a direct bond, $C_2$–$C_3$-alkylene or $C_2$–$C_3$-alkenylene, G is oxygen and $R^4$ and $R^5$ independently of one another are $C_1$–$C_5$-alkyl or $C_1$–$C_5$-alkoxy, or those wherein E is oxygen, Y and $R^1$ are hydrogen and $R^2$ and $R^3$ are methyl or methoxy.

The compounds embraced in a subgroup which is very particularly preferred are distinguished by the fact that E and G are oxygen, Y and $R^1$ are hydrogen, $R^2$ and $R^3$ are methyl or methoxy, the bridge $A_n$ is a direct bond, $C_2$–$C_3$-alkylene or $C_2$–$C_3$-alkenylene and $R^4$ and $R^5$ are $C_1$–$C_5$-alkyl or $C_1$–$C_5$-alkoxy.

The following should be mentioned as preferred individual compounds: N-[2-(diethoxyphosphonyl)-phenylsulfonyl]-N'-(4,6-dimethoxypyrimidin-2-yl)-urea and N-[2-(di-n-butoxyphosphonylvinyl)-phenylsulfonyl]-N'-(4-methoxy-6-methylpyrimidin-2-yl)-urea.

The compounds of the formula I are generally prepared in an inert, organic solvent.

The compounds of the formula I are obtained in a first process by reacting a phenylsulfonamide of the formula II

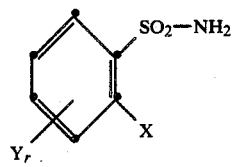

(II)

in which X, Y and r are as defined under formula I, in the presence of a base with an N-pyrimidinylcarbamate or N-triazinylcarbamate of the formula III

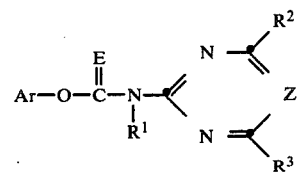

(III)

in which E, $R^1$, $R^2$, $R^3$ and Z are as defined under formula I and Ar is phenyl or phenyl which is substituted by $C_1$–$C_5$-alkyl, halogen, $C_1$–$C_5$-alkoxy or nitro.

Compounds of the formula I are obtained in a second process by reacting a phenylsulfonyl isocyanate or isothiocyanate of the formula IV

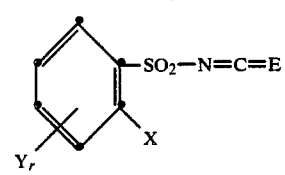

(IV)

in which E, X, Y and r are as defined under formula I, if appropriate in the presence of a base, with an amine of the formula V

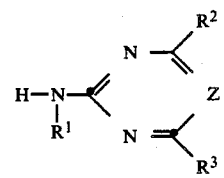

(V)

in which Z, $R^1$, $R^2$ and $R^3$ are as defined under formula I.

The resulting ureas of the formula I can, if desired, be converted into addition salts by means of amines, alkali metal or alkaline earth metal hydroxides or quaternary ammonium bases. This is effected, for example, by reaction with an equimolar amount of base and removal of the solvent by evaporation.

The reactions leading to compounds of the formula I are advantageously carried out in aprotic, inert organic solvents. Solvents of this type are hydrocarbons, such as benzene, toluene, xylene or cyclohexane, chlorinated hydrocarbons, such as methylene chloride, chloroform, carbon tetrachloride or chlorobenzene, ethers, such as diethyl ether, ethylene glycol dimethyl ether, diethylene glycol dimethyl ether, tetrahydrofuran or dioxane, nitriles, such as acetonitrile or propionitrile, or amides, such as dimethylformamide, diethylformamide or N-methylpyrrolidinone. The reaction temperatures are preferably between −20° and +120° C. In general, the reactions take place slightly exothermically and can be carried out at room temperature. It is advantageous to warm the reaction mixture to its boiling point for a short time in order to shorten the reaction time or to initiate the reaction. The reaction times can also be shortened by adding a few drops of a base or isocyanate as a catalyst for the reaction. Suitable bases are, in particular, tertiary amines, such as trimethylamine, triethylamine, quinuclidine, 1,4-diazabicyclo(2,2,2)octane, 1,5-diazabicyclo(4,3,0)non-5-ene or 1,5-diazabicyclo(5,4,0)undec-7-ene.

The end products of the formula I can be isolated by concentrating and/or evaporating the solvent, and can be purified by recrystallising or triturating the solid residue in solvents in which the end products are not readily soluble, such as ether, aromatic hydrocarbons or chlorinated hydrocarbons.

The starting materials of the formulae II and IV are novel. These compounds have been developed specially for the synthesis of the novel active substances of the formula I. They therefore form a part of the present invention.

The isocyanates or isothiocyanates of the formula IV can be obtained by methods known per se from the sulfonamides of the formula II, for example by treatment with phosgene or thiophosgene.

The starting materials of the formulae III and V are known or can be prepared by known methods.

The novel phosphorus-containing sulfonamides of the formula II can be prepared by methods known per se, depending on the nature of the ortho-substituent X. Such processes of preparation may be illustrated by mentioning the following reactions as examples:

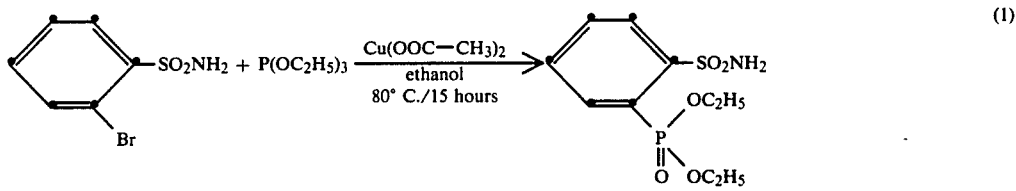
(1)

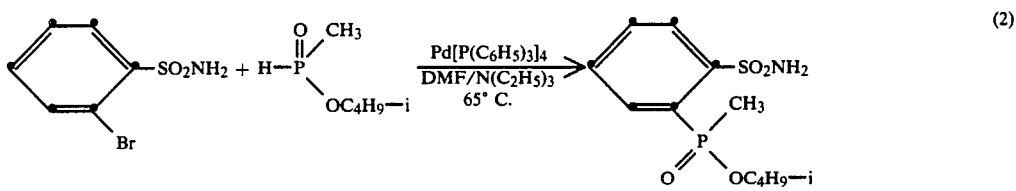
(2)

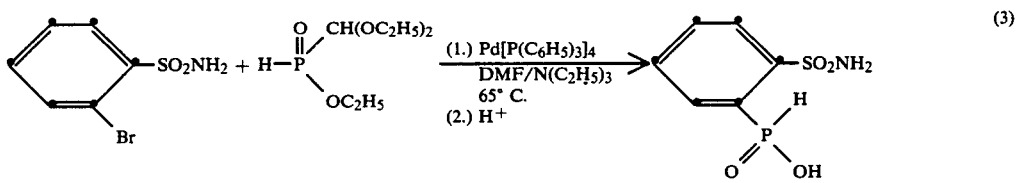
(3)

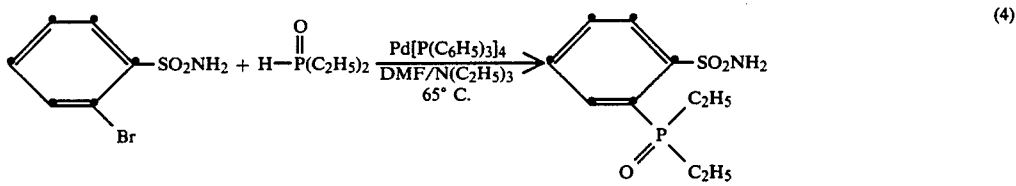
(4)

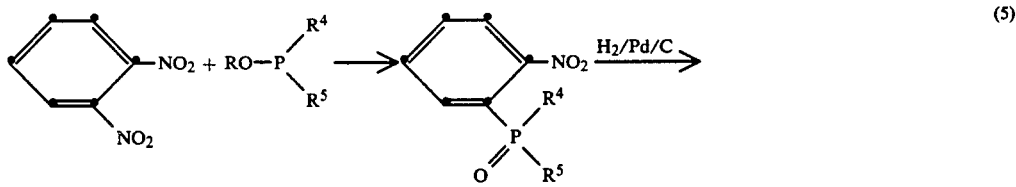
(5)

R = alkyl

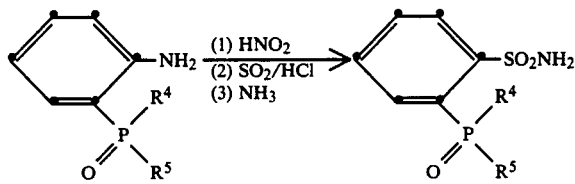

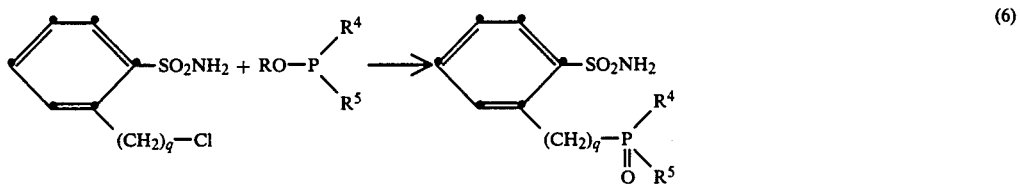
(6)

R = alkyl, q = 1 to 5

-continued
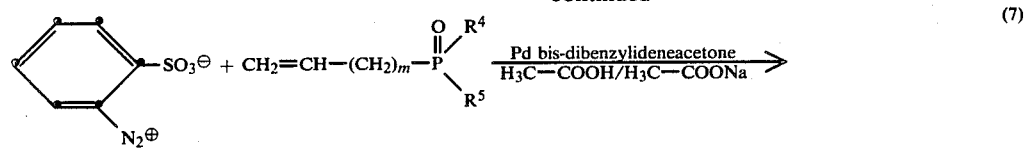 (7)
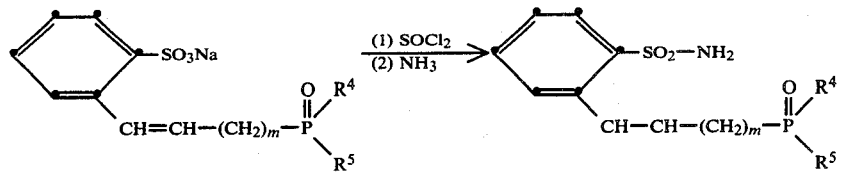
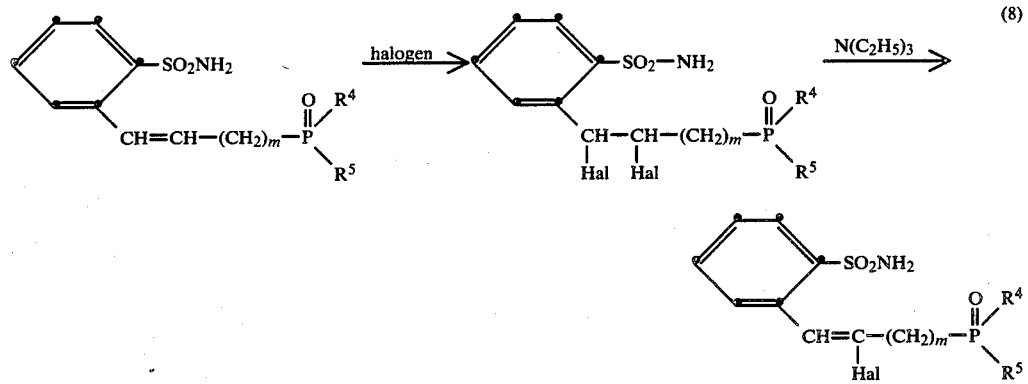 (8)
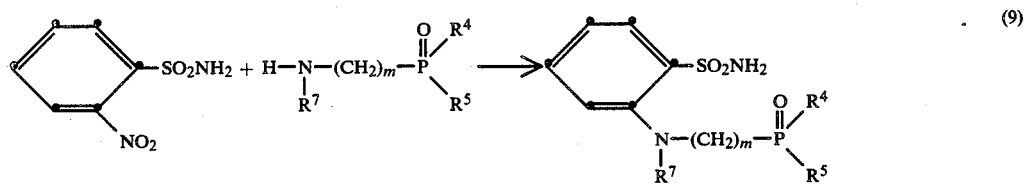 (9)
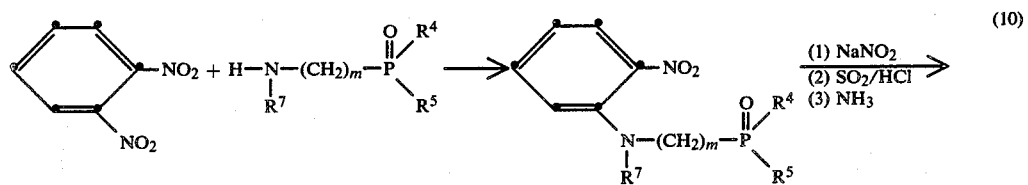 (10)
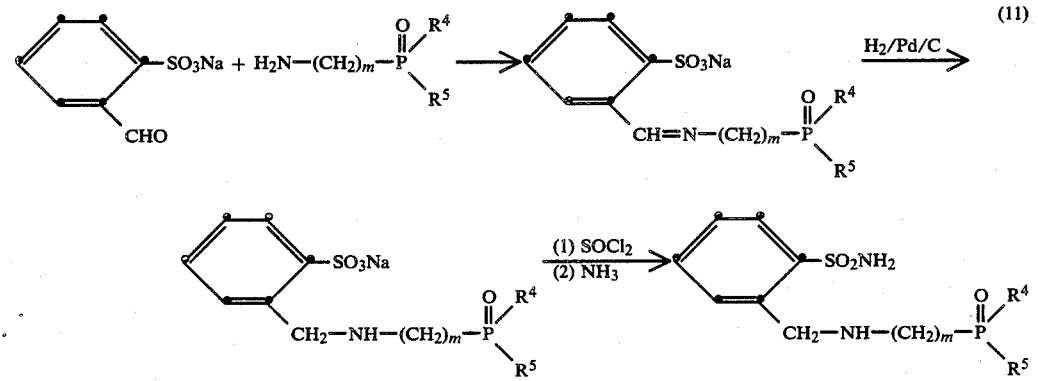 (11)

-continued

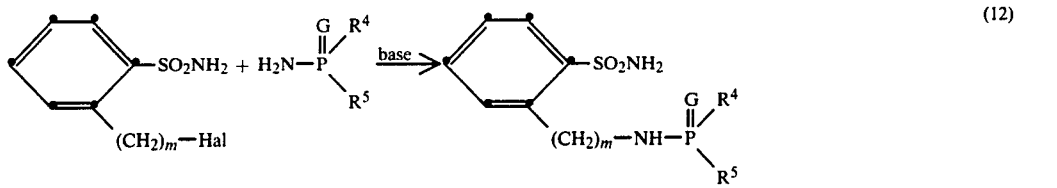

(12)

Hal = halogen

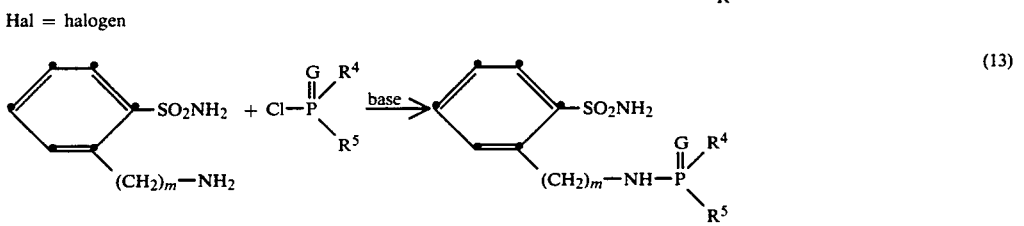

(13)

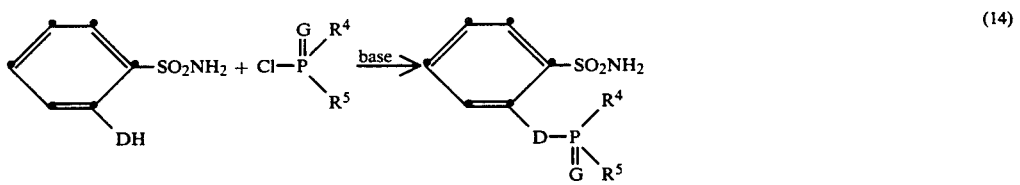

(14)

D = O, S

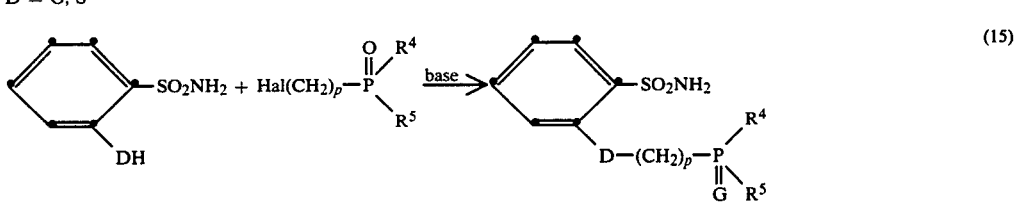

(15)

p = 0 to 2

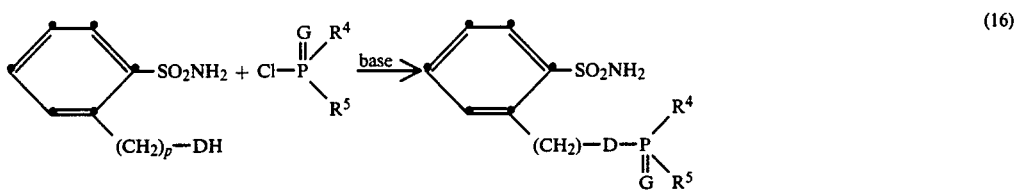

(16)

The active substances of the formula I are stable compounds. Their handling requires no precautionary measures.

At fairly low application rates, the compounds of the formula I are distinguished by good selective growth-inhibiting and selective herbicidal properties which make them excellently suitable for use in crops of useful plants, particularly in sugar cane, cereals, cotton, soya, maize and rice. In this application, damage is also caused in some cases to weeds which hitherto could only be controlled by means of total herbicides.

The mode of action of these active substances is unusual. Many are translocatable, i.e. they are absorbed by the plant and transported to other points, at which they then take effect. Thus it is possible, for example, to cause damage extending down to the roots of perennial weeds by surface treatment. In comparison with other herbicides and growth regulators, the novel compounds of the formula I are effective even at very low application rates.

In addition, the compounds of the formula I have powerful plant growth-regulating properties which can bring about an increase in the yield of crop plants or harvested material. In addition, many compounds of the formula I have a plant growth-inhibiting action which is dependent on the concentration. The growth of both monocotyledons and dicotyledons is adversely affected.

Thus it is possible, for example, to inhibit selectively, by means of the compounds of the formula I, the growth of the leguminosae which are frequently planted as "cover crops" (soil-covering crops) in agriculture in tropical regions, so that, although erosion of the soil between the crop plants is prevented, the "cover crops" do not become competitive with the crop.

In the case of many crop plants, inhibiting vegetative growth permits the crop to be planted more densely, so that an increased yield, based on the soil area, can be achieved.

A further mechanism for increasing yields by means of growth inhibitors is due to the fact that the nutrients benefit the formation of flowers and fruit to a greater extent, while vegetative growth is restricted.

In the case of monocotyledonous plants, for example grasses or crop plants, such as cereals, inhibition of vegetative growth is sometimes desirable and advantageous. Growth inhibition of this type is, inter alia, of economic interest in the case of grasses, since it is thus possible, for example, to reduce the frequency of cutting the grass in ornamental gardens, parks and sports grounds or on road verges. Another important aspect is the inhibition of the growth of herbaceous and woody plants on road verges and in the neighbourhood of overhead transmission lines or very generally in areas in which considerable ground vegetation is undesirable.

The use of growth regulators to inhibit the growth in length of cereals is likewise of importance, since the risk of the plants snapping off ("lodging") before the harvest is reduced or completely eliminated by shortening the stems. In addition, growth regulators can cause a strengthening of the stems of cereals, which also counteracts lodging.

The compounds of the formula I are also suitable for preventing the sprouting of stored potatoes. When potatoes are stored over the winter, sprouts frequently develop, resulting in shrinkage, loss of weight and rotting.

At fairly high application rates, the development of all the plants tested is damaged to such an extent that they die off.

The invention also relates to herbicidal and plant growth-regulating compositions containing a novel active compound of the formula I, and to processes for controlling weeds by the pre-emergence and post-emergence techniques and for inhibiting the plant growth of monocotyledonous and dicotyledonous plants, in particular grasses, tropical cover crops and tobacco side shoots.

The compounds of the formula I are employed as pure active substances or, preferably, as compositions together with the assistants conventionally used in the art of formulation and are, therefore, processed in a known manner to give, for example, emulsion concentrates, solutions which can be atomised or diluted without further treatment, dilute emulsions, wettable powders, soluble powders, dusting agents, granules and encapsulations in, for example, polymeric substances. The application processes, such as spraying, atomising, dusting, sprinkling or watering, are selected to suit the intended aims and the given circumstances, as is also the nature of the compositions.

The formulations, i.e. the compositions, preparations or combinations containing the active substance of the formula I and, if appropriate, a solid or liquid adjuvant, are prepared in a known manner, for example by intimately mixing and/or grinding the active substances with extenders, for example with solvents, solid carriers and, if appropriate, surface-active compounds (surfactants).

The following can be suitable as solvents: aromatic hydrocarbons, preferably the fractions from $C_8$ to $C_{12}$, for example mixed xylenes or substituted naphthalenes, phthalic acid esters, such as dibutyl or dioctyl phthalate, aliphatic hydrocarbons, such as cyclohexane or paraffins, alcohols and glycols and also ethers and esters thereof, such as ethanol, ethylene glycol or ethylene glycol monomethyl or monoethyl ether, ketones, such as cyclohexanone, strongly polar solvents, such as N-methyl-2-pyrrolidone, dimethyl sulfoxide or dimethylformamide, and vegetable oils which can be epoxidised, such as epoxidised coconut oil or soya oil; or water.

The solid carriers used, for example, for dusting compositions and dispersible powders, are, as a rule, natural ground minerals, such as calcite, talc, kaolin, montmorrilonite or attapulgite. It is also possible to add highly disperse silica or highly disperse absorbant polymers in order to improve the physical properties. Suitable particulate, adsorptive granular carriers are porous types, for example pumice stone, broken brick, sepiolite or bentonite, while examples of suitable non-sorptive carriers are calcite or sand. In addition, it is possible to use a large number of pregranulated materials of an inorganic or organic nature, such as, in particular, dolomite or comminuted plant residues.

Depending on the nature of the active substance of the formula I to be formulated, suitable surface-active compounds are non-ionic, cationic and/or anionic surfactants having good emulsifying, dispersing and wetting properties. Surfactants are also to be understood as meaning mixtures of surfactants.

Suitable anionic surfactants can be so-called water-soluble soaps as well as water-soluble synthetic surface-active compounds.

Soaps which may be mentioned are the alkali metal salts, alkaline earth metal salts or substituted or unsubstituted ammonium salts of higher fatty acids ($C_{10}$–$C_{22}$), for example the Na or K salts of oleic or stearic acid, or of natural mixtures of fatty acids, which can be obtained, for example, from coconut oil or tallow oil. Furthermore, mention should also be made of the salts of fatty acid methyltaurides.

Frequently, however, so-called synthetic surfactants are used, in particular fatty sulfonates, fatty sulfates, sulfonated benzimidazole derivatives or alkylarylsulfonates.

The fatty sulfonates or sulfates are, as a rule, in the form of alkali metal salts, alkaline earth metal salts or substituted or unsubstituted ammonium salts, and contain an alkyl radical having 8 to 22 C atoms, in which connection alkyl also includes the alkyl moiety of acyl radicals, for example the Na or Ca salt of ligninsulfonic acid, of dodecylsulfuric acid ester or of a mixture of fatty alcohol sulfates prepared from natural fatty acids. These products also include the salts of the sulfuric acid esters and sulfonic acids of fatty alcohol/ethylene oxide adducts. The sulfonated benzimidazole derivatives preferably contain 2 sulfonic acid groups and a fatty acid radical having 8–22 C atoms. Examples of alkylarylsulfonates are the Na, Ca or triethanolamine salts of dodecylbenzenesulfonic acid, of dibutylnaphthalenesulfonic acid or of a naphthalenesulfonic acid/formaldehyde condensation product.

Furthermore, corresponding phosphates, for example salts of the phosphoric acid ester of a p-nonylphenol/(4-14)ethylene oxide adduct, or phospholipids are also suitable. Suitable non-ionic surfactants are primarily polyglycol ether derivatives of aliphatic or cycloaliphatic alcohols, saturated or unsaturated fatty acids and alkylphenols, and these derivatives can contain 3 to 30 glycol ether groups and 8 to 20 carbon atoms in the (aliphatic) hydrocarbon radical and 6 to 18 carbon atoms in the alkyl radical of the alkylphenols.

Further suitable non-ionic surfactants are the water-soluble adducts, containing 20 to 250 ethylene glycol ether groups and 10 to 100 propylene glycol ether groups, of polyethylene oxide with polypropylene glycol, ethylenediaminopolypropylene glycol and an alkylpolypropylene glycol having 1 to 10 carbon atoms in the alkyl chain. The said compounds usually contain 1 to 5 ethylene glycol units per unit of propylene glycol.

Examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylenesorbitan, such as polyoxyethylenesorbitan trioleate, are also suitable.

The cationic surfactants are, in particular, quaternary ammonium salts which contain, as N-substituents, at least one alkyl radical having 8 to 22 C atoms and, as further substituents, lower, halogenated or non-halogenated alkyl radicals, benzyl radicals or lower hydroxyalkyl radicals. The salts are preferably in the form of halides, methylsulfates or ethylsulfates, for example stearyltrimethylammonium chloride or benzyl-di-(2-chloroethyl)-ethylammonium bromide.

The surfactants which are conventionally used in the art of formulation are described, inter alia, in the following publications:

"McCutcheon's Detergents and Emulsifiers Annual", MC Publishing Corp., Ridgewood, N.J., 1981; H. Stache, "Tensid-Taschenbuch" ["Surfactants Handbook"], 2nd Edition, C. Hanser Verlag, Munich, Vienna, 1981; M. and J. Ash, "Encyclopedia of Surfactants", Vol. I–III, Chemical Publishing Co., New York, 1980–1981.

The pesticidal preparations contain, as a rule, 0.1 to 95%, in particular 0.1 to 80%, of an active substance of the formula I, 1 to 99.9% of a solid or liquid adjuvant and 0 to 25%, in particular 0.1 to 25%, of a surfactant.

In particular, preferred formulations have the following composition: (%=per cent by weight)

| Emulsifiable concentrates | |
|---|---|
| Active substance: | 1 to 20%, preferably 5 to 10% |
| Surface-active agents: | 5 to 30%, preferably 10 to 20% |
| Liquid carrier: | 50 to 94%, preferably 70 to 85%. |
| Dusts | |
| Active substance: | 0.1 to 10%, preferably 0.1 to 1% |
| Solid carrier: | 99.9 to 90%, preferably 99.9 to 99%. |
| Suspension concentrates | |
| Active substance: | 5 to 75%, preferably 10 to 50% |
| Water: | 94 to 25%, preferably 90 to 30% |
| Surface-active agent: | 1 to 40%, preferably 2 to 30%. |
| Wettable powders | |
| Active substance: | 0.5 to 90%, preferably 1 to 80% |
| Surface-active agent: | 0.5 to 20%, preferably 1 to 15% |
| Solid carrier: | 5 to 95%, preferably 15 to 90%. |
| Granules | |
| Active substance: | 0.5 to 30%, preferably 3 to 15% |
| Solid carrier: | 99.5 to 70%, preferably 97 to 85%. |

Whereas concentrated compositions are more likely to be preferred as commercial products, the final consumer as a rule uses dilute compositions. The use formulations can be diluted down to 0.001% of active substance. The application rates are as a rule 0.001 to 10 kg of active substance per hectare, preferably 0.025 to 5 kg of active substance per hectare.

The compositions can also contain further additives, such as stabilisers, anti-foaming agents, viscosity regulators, binders, tackifiers and fertilisers or other active substances for achieving special effects.

In the examples which follow, the temperatures are quoted in degrees centigrade, °C., and the pressure in millibar, mb.

PREPARATION EXAMPLES

EXAMPLE 1

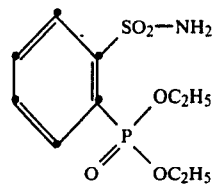

2-Diethoxyphosphonylphenylsulfonamide 59 g (0.25 mole) of 2-bromophenylsulfonamide are dissolved in 1 liter of ethanol and the solution is treated with 55 g (0.275 mole) of hydrated copper-II acetate and 62 g (0.37 mole) of triethyl phosphite and heated at reflux temperature for 15 hours, in the course of which the solution changes from a deep blue colour to blue-green. After cooling, the solution is filtered and evaporated. The residue is taken up in 200 ml of chloroform and the solution is washed with twice 200 ml of water. After the organic phase has been evaporated, the orange-brown residue is crystallised from ether. This gives 16.3 g (22.3% of theory) of 2-diethoxyphosphonylphenylsulfonamide, melting point 164°–165° C.

EXAMPLE 2

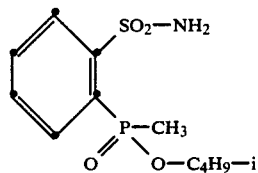

2-(i-Butoxy-P-methylphosphinyl)-phenylsulfonamide

A solution of 11.8 g (0.05 mole) of 2-bromophenylsulfonamide in 14 ml (0.1 mole) of triethylamine and 30 ml of dimethylformamide is treated with 6.8 g (0.05 mole) of isobutyl methylphosphinate and 1.1 g (0.001 mole) of tetrakistriphenylphosphine-palladium complex. The yellow suspension is stirred for 15 hours at 100° C., cooled and filtered. After the filtrate has been evaporated, the residue is crystallised from toluene. This gives 4.12 g of 2-(i-butoxy-P-methylphosphinyl)-phenylsulfonamide, melting point 50°–52° C.

EXAMPLE 3

2-Diethoxyphosphonylphenylsulfonamide (a) 2-Diethoxyphosphonylnitrobenzene:

A mixture of 63 g (0.375 mole) of 1,2-dinitrobenzene and 131.2 ml (0.375 mole) of triethyl phosphite in 350 ml of toluene is heated at reflux temperature for 7 hours and is then evaporated. The oily residue is fractionated in vacuo. The fraction having a boiling point of 136°–145° C./0.05 mbar is taken up in 100 ml of methylene chloride, and 200 ml of hexane are then added. The crystals thus precipitated are separated off, washed with hexane and dried. This gives 58.8 g (60.5% of theory) of 2-diethoxyphosphonylnitrobenzene in the form of pale yellow crystals, melting point 56.5°–57.5° C.

$^1$H-NMR (CDCl$_3$): δ=1.33 (t, CH$_3$, 6H); 4.23 (quintet, OCH$_2$, 4H); 7.5–8.3 (m, C$_6$H$_4$, 4H) ppm.

Analysis for $C_{10}H_{14}NO_5P$ (259.2): calculated: C 46.34%, H 5.45%, N 5.40%, found: C 46.2%, H 5.4%, N 5.5%.

(b) 2-Diethoxyphosphonylaniline:

58.3 g of 2-diethoxyphosphonylnitrobenzene are dissolved in 590 ml of ethanol and hydrogenated with hydrogen over 3 g of 5% palladium-on-charcoal at 20°-25° C. 104% of the theoretical amount of hydrogen has been consumed after 20 minutes, and the hydrogenation is complete. After the catalyst has been removed, the filtrate is evaporated. Crystallising the residue from hexane at 0° C. gives 48.2 g (42.7% of theory) of 2-diethoxyphosphonylaniline, melting point 32°-34° C.

$^1H$-NMR (CDCl$_3$): $\delta$=1.30 (t, CH$_3$, 6H); 4.1 (quintet, OCH$_2$, 4H); 5.15 (s, NH$_2$, 2H); 6.5-7.7 (m, C$_6$H$_4$, 4H) ppm.

(c) 2-Diethoxyphosphonylphenylsulfonamide:

1.145 g of 2-diethoxyphosphonylaniline, 1.05 ml of 36% hydrochloric acid and 0.78 ml of water are mixed together with cooling. A solution of 0.357 g of sodium nitrite in 0.537 ml of water is added dropwise at 0°-5° C. to the resulting solution in the course of 20 minutes, and the mixture is stirred at the same temperature for 35 minutes. The resulting solution is added, in the course of 15 minutes and in step with 0.95 ml of a 40% aqueous solution of sodium bisulfite, to a mixture of 3.45 ml of 36% hydrochloric acid and 0.875 ml of water, 0.126 g (0.005 mole) of hydrated copper sulfate and 0.95 ml of 40% aqueous sodium bisulfite solution. The reaction mixture is stirred for 1.5 hours at 20°-25° C. and is extracted three times with methylene chloride. The combined organic phases are washed twice with water, dried over sodium sulfate and evaporated. This gives 1.5 g of 2-diethoxyphosphonylphenylsulfonyl chloride in the form an oil, which, without purification, is reacted with 10.6 ml of 30% aqueous ammonia solution at 20°-25° C.. The resulting precipitate is separated off and washed with water.

Yield: 0.7 g of 2-diethoxyphosphonylphenylsulfonamide, melting point 161°-162° C.

EXAMPLE 4

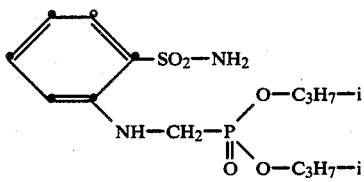

2-(Di-i-propoxyphosphonylmethylamino)-phenylsulfonamide 10 g (0.58 mole) of 2-nitrophenylsulfonamide are suspended in 20 ml of toluene and heated to reflux temperature. 17.0 g (0.087 mole) of diisopropyl aminomethylphosphonate are added dropwise to the hot solution. The reaction mixture is then boiled under reflux for 10 hours, cooled and evaporated. Chromatographing the residue over silica gel with a 4:1 methyl acetate/hexane mixture gives 1.6 g of 2-(di-i-propoxyphosphonylmethylamino)-phenylsulfonamide in the form of a yellow oil.

$^1H$-NMR (CDCl$_3$): $\delta$1.30 (d, CH$_3$, 12H); 3.6 (2d, J$_P$CH=14 Hz, J$_N$HCH=6 Hz, 2H); 4.7 (m, OCH, 2H); 6.6-7.9 (m, C$_6$H$_4$, 4H); 8.0-8.3 (m, NH, NH$_2$, 3H) ppm.

EXAMPLE 5

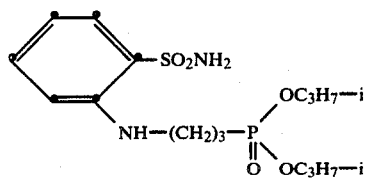

2-(Di-i-propoxyphosphonylpropylamino)-phenylsulfonamide (a) 2-(Di-i-propoxyphosphonylpropylamino)-nitrobenzene:

A mixture of 20 g (0.11 mole) of 1,2-dinitrobenzene and 31.87 g (0.14 mole) of diisopropyl aminopropylphosphonate in 50 ml of toluene is heated at reflux temperature for 14 hours and is then evaporated. Chromatographing the residue over silica gel using a 4:1 ethyl acetate/hexane mixture gives 32.04 g (84.6% of theory) of 2-(di-i-propoxyphosphonylpropylamino)-nitrobenzene in the form of a dark yellow viscous oil.

$^1$H-NMR (CDCl$_3$): $\delta$=1.4 (d, CH$_3$, 12H); 2.0 (s, broad, CH$_2$, CH$_2$P, 4H); 3.5 (q, NH$_2$, 2H); 4.75 (m, OCH, 2H); 6.5-8.3 (s, broad, C$_6$H$_4$, NH, 5H) ppm.

(b) 2-(Di-i-propoxyphosphonylpropylamino)-aniline 2-(Di-i-propoxyphosphonylpropylamino)-aniline is obtained, in the form a viscous oil, as the product from 5a and hydrogen in the presence of 5% Pd/C by the process described in Example 3a.

EXAMPLE 6

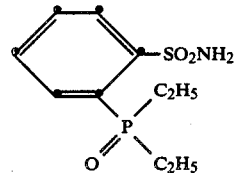

2-Diethylphosphonylphenylsulfonamide

2-Diethylphosphonylphenylsulfonamide, melting point 139° C., is obtained as the product from 2-bromophenylsulfonamide and diethylphosphine oxide in the presence of triethylamine, dimethylformamide and tetrakistriphenylphosphinepalladium complex, by the process described in Example 2.

EXAMPLE 7

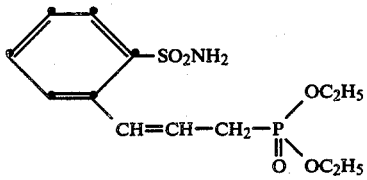

2-(3-Diethoxyphosphonyl-1-propenyl)-phenylsulfonamide (a) A mixture of 34.64 g (0.2 mole) of orthanilic acid, 30 ml of water and 62.3 ml of 50% fluoboric acid (0.5 mole) is cooled to 0°-5° C. and is treated, at this temperature, with a solution of 13.8 g (0.2 mole) of sodium nitrite in 20 ml of water, added dropwise in the course of one hour. The mixture is then stirred for 30 minutes and taken up in 100 ml of ether. The precipitate which has been deposited is separated off and washed with 100 ml of a 1:1 acetic acid/ether mixture and 100 ml of ether. After drying, 34 g of orthanilic acid diazonium salt (92% of theory) are thus obtained.

(b) A mixture of 8.65 g (0.05 mole) of orthanilic acid, 50 ml of acetic acid and 6.25 ml (0.05 mole) of fluoboric acid is cooled to approx. 15° C. and is treated at this temperature with a solution of 3.45 g (0.05 mole) of sodium nitrite in 5 ml of water, added dropwise in the course of 45 minutes. The resulting reaction mixture is stirred for 30 minutes at 20°–25° C. The suspension can be employed for the following reaction without further isolation of the diazonium salt.

(c) 7.73 g (0.042 mole) of the diazonium salt of orthanilic acid prepared in accordance with Example 7a are suspended in 50 ml of acetic acid and treated with 3.44 g (0.042 mole) of sodium acetate and 0.1265 g (0.00021 mole) of palladium dibenzylideneacetone. 7.85 g (0.044 mole) of diethyl propenyl-3-phosphonate are added dropwise to this mixture at 20°–25° C. The reaction sets in with the liberation of heat and evolution of nitrogen. The reaction mixture is stirred for a further 1.5 hours when the evolution of gas ceases. The solvent is then removed completely. The residue obtained is taken up in 50 ml of dimethylformamide and treated dropwise with 7.64 ml (0.105 mole) of thionyl chloride at a temperature of 5°–10° C. After a reaction time of 2 hours, the mixture is poured onto ice and extracted with ethyl acetate. The combined organic phases are washed with water and then added dropwise to a mixture of 25 ml of concentrated ammonia and ice. When the reaction is complete, the mixture is diluted with water and the organic phase is separated off. Chromatography over silica gel using a 1:1 toluene/ethyl acetate mixture gives 2.28 g (16% of theory) of 2-(3-diethoxyphosphonyl-1-propenyl)-phenylsulfonamide, melting point 103°–104° C.

Analysis for $C_{13}H_{20}NO_5PS$ (333.34): calculated: C 46.85%, H 6.05%, N 4.20%, P 9.30%, S 9.62%, found: C 46.93%, H 6.04%, N 4.13%, P 9.25%, S 9.38%.

EXAMPLE 8

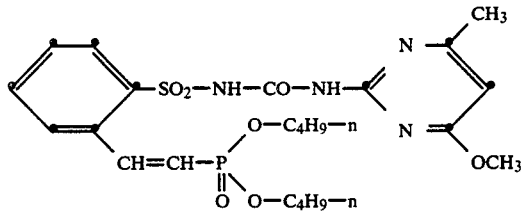

N-[2-(Di-n-butoxyphosphonylvinyl)-phenylsulfonyl]-N'-(4-methoxy-6-methylpyrimidin-2-yl)-urea. (Compound 4.1)

(a) 2-(Di-n-butoxyphosphonylvinyl)-phenylsulfonamide 11.04 g (0.06 mole) of the diazonium salt obtained following the instructions of Example 7a are suspended in 70 ml of acetic acid and treated with 13.2 g of di-n-butyl vinylphosphonate in the presence of 4.29 g (0.06 mole) of sodium acetate and 0.182 g (0.003 mole) of palladium dibenzylideneacetone. When the evolution of nitrogen is complete, the mixture is stirred for a further ½ hour. The solvent is then removed by evaporation and the residue is taken up in 40 ml of dimethylformamide, 10.91 ml (0.15 mole) of thionylchloride are added, and the mixture is stirred for 1.5 hours at 5° C. The reaction mixture is then poured onto ice and extracted with ethyl acetate. The combined ethyl acetate phases are added dropwise to 20 ml of concentrated ammonia solution and 20 g of ice. When the reaction is complete, the organic phase is separated off, washed with water, dried and evaporated. Chromatographing the oily residue over silica gel with a 4:1 toluene/ethyl acetate mixture gives 13.72 g (61% of theory) of 2-(di-n-butoxyphosphonylvinyl)-phenylsulfonamide in the form a viscous oil.

Analysis for $C_{16}H_{26}NO_5PS$ (375.42): calculated: C 51.19%, H 6.98%, N 3.73%, P 8.25%, S 8.54%, found: C 51.28%, H 7.09%, N 3.60%, P 8.02%, S 8.41%, (b) 2.4 ml (0.0165 mole) of 1,5-diazabicyclo(5,4,0)undec-5-ene and 3.9 g (0.015 mole) of phenyl N-(4-methoxy-6-methylpyrimidin-2-yl)-carbamate are added at 20°–25° C. to a solution of 5.63 g (0.015 mole) of 2-(di-n-butoxyphosphonylvinyl)phenylsulfonamide in 80 ml of dioxane. After the mixture has been stirred for 2 hours, it is poured onto 200 ml of water. The clear solution formed is acidified to a pH value of 2 with 36% hydrochloric acid and is extracted with methyl acetate. The combined organic phases are dried and evaporated. Crystallising the orange oily residue from petroleum ether gives 6.9 g (85.2% of theory) of N-[2-(di-n-butoxyphosphonylvinyl)-phenylsulfonyl]-N'-(4-methoxy-6-methylpyrimidin-2-yl)urea, melting point 86°–87° C.

EXAMPLE 9

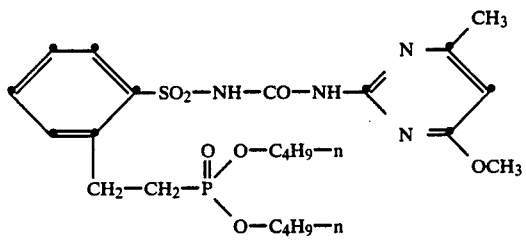

N-[2-(Di-n-butoxyphosphonylethyl)-phenylsulfonyl]-N'-(4-methoxy-6-methylpyrimidin-2-yl)-urea. (Compound 4.21)

4.0 g (0.074 mole) of N-[2-(di-n-butoxyphosphonylvinyl)-phenylsulfonyl]-N'-(4-methoxy-6-methylpyrimidin-2-yl)urea are dissolved in 40 ml of tetrahydrofuran and hydrogenated with hydrogen at 20°–25° C., with the addition of 0.5 g of platinum hydroxide. The reaction comes to a standstill when 114% of the amount of hydrogen theoretically required has been absorbed. The catalyst is filtered off and the solution is evaporated. The colourless residue is crystallised from ether. This gives 4.0 g (100% of theory) of N-[2-(di-n-butoxyphosphonylethyl)-phenylsulfonyl]-N'-(4-methoxy-6-methylpyrimidin-2-yl)-urea, melting point 97°–98° C.

EXAMPLE 10

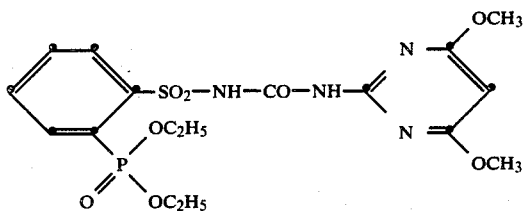

N-(2-Diethoxyphosphonylphenylsulfonyl)-N'-(4,6-dimethoxypyrimidin-2-yl)-urea. (Compound 4.31)

1.7 g of 2-diethoxyphosphonylphenylsulfonamide and 0.9 g of 1,5-diazabicyclo(5,4,0)undec-5-ene are dissolved in 19 ml of dioxane and treated with 1.6 g of phenyl N-(4,6-dimethoxypyrimidin-2-yl)-carbamate. When the solution has been stirred at 20°–25° C. for 5 hours, 100 ml of ethyl acetate are added. The solution is acidified to a pH value of 2 by adding 2N hydrochloric acid, in the course of which the product is partially precipitated. The aqueous phase is separated off and the organic phase is washed twice with water. After the organic phase has been evaporated, the residue is crystallised from an acetone/ether mixture. This gives 2.5 g (90.8% of theory) of N-(2-diethoxyphosphonylphenylsulfonyl)-N'-(4,6-dimethoxypyrimidin-2-yl)-urea, melting point 172° C. (decomposition).

Analysis for $C_{17}H_{23}N_4O_8PS$ (474.43): calculated: C 43.04%, H 4.89%, N 11.81%, P 6.53%, S 6.76%, found: C 43.5%, H 4.6%, N 12.1%, P 6.6%, S 6.6%.

The intermediates and end products listed in the tables below are obtained analogously.

TABLE 1

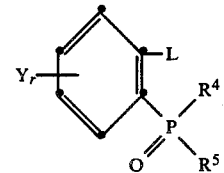

| No. | $R_4$ | $R_5$ | L | Y | r | Physical data |
|---|---|---|---|---|---|---|
| 1.1 | $OC_2H_5$ | $OC_2H_5$ | $NO_2$ | H | 1 | m.p. 56.5–57.5° C. |
| 1.2 | $OC_2H_5$ | $OC_2H_5$ | $NH_2$ | H | 1 | m.p. 32–34° C. |
| 1.3 | $OC_2H_5$ | $CH_3$ | $NO_2$ | H | 1 | m.p. 129° C./0.08 mb |
| 1.4 | $OC_2H_5$ | $OC_2H_5$ | $NO_2$ | 5-Cl | 1 | m.p. 61–62° C. |
| 1.5 | $OC_2H_5$ | $CH_3$ | $NO_2$ | 5-Cl | 1 | m.p. 151–152° C./0.26 mb |
| 1.6 | OH | OH | $NO_2$ | H | 1 | m.p. 197–199° C. |
| 1.7 | OH | $CH_3$ | $NO_2$ | H | 1 | m.p. 147–149° C. |
| 1.8 | OH | OH | $NO_2$ | 5-Cl | 1 | m.p. 208–210° C. |
| 1.9 | OH | $CH_3$ | $NO_2$ | 5-Cl | 1 | m.p. 150–151° C. |
| 1.10 | $OC_2H_5$ | $CH_3$ | $NH_2$ | 4-$CF_3$, 6-$NO_2$ | 2 | m.p. 117–119° C. |
| 1.11 | $OC_2H_5$ | $CH_3$ | $NO_2$ | 4-$CF_3$, 6-$NO_2$ | 2 | m.p. 130–132° C. |
| 1.12 | $C_6H_5$ | OH | $NO_2$ | 4-$CF_3$, 6-$NO_2$ | 2 | m.p. 133–138° C. |
| 1.13 | $C_6H_5$ | $OC_4H_9$—n | $NO_2$ | 4-$CF_3$, 6-$NO_2$ | 2 | m.p. 89–90° C. |
| 1.14 | $C_6H_5$ | $C_6H_5$ | $NO_2$ | 4-$CF_3$, 6-$NO_2$ | 2 | m.p. 188–190° C. |
| 1.15 | $OC_2H_5$ | $OC_2H_5$ | $NH_2$ | 5-Cl | 1 | m.p. 72–75° C. |
| 1.16 | $OC_2H_5$ | $OC_2H_5$ | $NO_2$ | 4-CN, 6-$NO_2$ | 2 | m.p. 109–112° C. |
| 1.17 | $OC_2H_5$ | $OC_2H_5$ | $NO_2$ | 4-$COOC_2H_5$ | 1 | brown oil |
| 1.18 | OH | OH | $NO_2$ | 4-COOH | 1 | m.p. 220° C. |
| 1.19 | OH | OH | $NO_2$ | 4-$COOC_2H_5$ | 1 | m.p. 184–186° C. |

TABLE 2

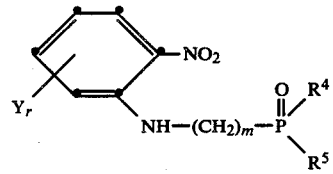

| No. | $R^4$ | $R^5$ | Y | r | m | Physical data |
|---|---|---|---|---|---|---|
| 2.1 | $OC_3H_7$—i | $OC_3H_7$—i | H | 1 | 3 | yellow oil |
| 2.2 | $OC_2H_5$ | $OC_2H_5$ | H | 1 | 1 | m.p. 81–83° C. |
| 2.3 | OH | OH | H | 1 | 3 | m.p. 142–145° C. |
| 2.4 | OH | OH | H | 1 | 1 | m.p. 147–148° C. |
| 2.5 | $OC_2H_5$ | $OC_2H_5$ | H | 1 | 2 | orange oil |
| 2.6 | $OC_2H_5$ | $OC_2H_5$ | 5-Cl | 1 | 1 | orange oil |
| 2.7 | $OC_2H_5$ | $OC_2H_5$ | 5-Cl | 1 | 2 | highly viscous oil |
| 2.8 | OH | OH | H | 1 | 2 | m.p. 124–127° C. |
| 2.9 | $OC_3H_7$—i | $OC_3H_7$—i | 5-Cl | 1 | 3 | viscous oil |
| 2.10 | OH | OH | 5-Cl | 1 | 3 | m.p. 218° C. |
| 2.11 | $OC_3H_7$—i | $OC_3H_7$—i | 4-$COOC_2H_5$ | 1 | 1 | m.p. 73–74° C. |
| 2.12 | OH | OH | 4-COOH | 1 | 1 | m.p. 270° C. |
| 2.13 | OH | OH | 4-$COOC_2H_5$ | 1 | 1 | yellow oil |

TABLE 3

[Structure: benzene ring with -SO₂NH₂, X, and Y_r substituents]

| No. | X | Y | r | Physical data |
|---|---|---|---|---|
| 3.1 | —PO(OC₂H₅)₂ | H | 1 | m.p. 164–165° C. |
| 3.2 | —PO(CH₃)—OC₄H₉—i | H | 1 | m.p. 50–52° C. |
| 3.3 | —PO(C₂H₅)₂ | H | 1 | m.p. 139° C. |
| 3.4 | —CH=CH—CH₂—PO(OC₂H₅)₂ | H | 1 | m.p. 103–104° C. |
| 3.5 | —CH=CH—PO(OC₄H₉—n)₂ | H | 1 | viscous oil |
| 3.6 | —(CH₂)₃—PO(OC₂H₅)₂ | H | 1 | |
| 3.7 | —(CH₂)₂—PO(OC₂H₅)₂ | H | 1 | |
| 3.8 | —CH₂—PO(OC₂H₅)₂ | H | 1 | m.p. 110–117° C. |
| 3.9 | —NH—CH₂—PO(OC₃H₇—i)₂ | H | 1 | |
| 3.10 | —NH—(CH₂)₂—PO(OC₃H₇—i)₂ | H | 1 | |
| 3.11 | —NH—(CH₂)₃—PO(OC₃H₇—i)₂ | H | 1 | |
| 3.12 | —NH—(CH₂)₂—PO(OC₂H₅)₂ | H | 1 | |
| 3.13 | —PO(OC₂H₅)₂ | 5-Cl | 1 | |
| 3.14 | —PO(CH₃)—OC₂H₅ | 5-Cl | 1 | |
| 3.15 | —PO(CH₃)—OC₂H₅ | H | 1 | |
| 3.16 | —PO(OH)₂ | H | 1 | |
| 3.17 | —PO(OH)₂ | 5-Cl | 1 | |
| 3.18 | —PO(OC₂H₅)₂ | 4-CF₃, 6-NO₂ | 2 | |
| 3.19 | —PO(CH₃)—OC₂H₅ | 4-CF₃, 6-NH₂ | 2 | |
| 3.20 | —PO(CH₃)—OC₂H₅ | 4-CF₃, 6-NO₂ | 2 | |
| 3.21 | —PO(OC₂H₅)₂ | 4-COOC₂H₅ | 1 | |
| 3.22 | —NH—(CH₂)₃—PO(OC₂H₅)₂ | 5-Cl | 1 | |
| 3.23 | —NH—(CH₂)₃—PO(OC₃H₇—i)₂ | 5-Cl | 1 | |
| 3.24 | —NH—CH₂—PO(OC₂H₅)₂ | H | 1 | |

TABLE 4

[Structure: benzene ring with -SO₂-NH-CO-NH- linked to heterocycle containing R², R³, Z, and X, Y_r substituents]

| No. | R² | R³ | X | Y | r | Z | Physical data |
|---|---|---|---|---|---|---|---|
| 4.1 | CH₃ | OCH₃ | —CH=CH—PO(OC₄H₉—n)₂ | H | 1 | CH | m.p. 86–87° C. |
| 4.2 | CH₃ | CH₃ | —CH=CH—PO(OC₄H₉—n)₂ | H | 1 | CH | |
| 4.3 | CH₃ | CH₃ | —CH=CH—PO(OC₄H₉—n)₂ | H | 1 | N | |
| 4.4 | OCH₃ | OCH₃ | —CH=CH—PO(OC₄H₉—n)₂ | H | 1 | N | |
| 4.5 | OCH₃ | OCH₃ | —CH=CH—PO(OC₂H₉—n)₂ | H | 1 | CH | |
| 4.6 | CH₃ | OCH₃ | —CH=CH—CH₂—PO(OC₂H₅)₂ | H | 1 | N | m.p. 153–154° C. |
| 4.7 | OCH₃ | OCH₃ | —CH=CH—CH₂—PO(OC₂H₅)₂ | H | 1 | N | |
| 4.8 | CH₃ | OCH₃ | —CH=CH—CH₂—PO(OC₂H₅)₂ | H | 1 | CH | |
| 4.9 | CH₃ | CH₃ | —CH=CH—CH₂—PO(OC₂H₅)₂ | H | 1 | CH | |
| 4.10 | OCH₃ | OCH₃ | —CH=CH—CH₂—PO(OC₂H₅)₂ | H | 1 | CH | |
| 4.11 | CH₃ | OCH₃ | —PO(CH₃)—OC₄H₉—i | H | 1 | CH | |
| 4.12 | CH₃ | CH₃ | —PO(CH₃)—OC₄H₉—i | H | 1 | CH | |
| 4.13 | OCH₃ | OCH₃ | —PO(CH₃)—OC₄H₉—i | H | 1 | CH | |
| 4.14 | CH₃ | OCH₃ | —PO(CH₃)—OC₄H₉—i | H | 1 | N | |
| 4.15 | OCH₃ | OCH₃ | —PO(CH₃)—OC₄H₉—i | H | 1 | N | |
| 4.16 | CH₃ | OCH₃ | —PO(C₂H₅)₂ | H | 1 | CH | |
| 4.17 | OCH₃ | OCH₃ | —PO(C₂H₅)₂ | H | 1 | CH | |
| 4.18 | CH₃ | CH₃ | —PO(C₂H₅)₂ | H | 1 | CH | |
| 4.19 | CH₃ | OCH₃ | —PO(C₂H₅)₂ | H | 1 | N | |
| 4.20 | OCH₃ | OCH₃ | —PO(C₂H₅)₂ | H | 1 | N | |
| 4.21 | CH₃ | OCH₃ | —(CH₂)₂—PO(OC₄H₉—n)₂ | H | 1 | CH | m.p. 97–98° C. |
| 4.22 | CH₃ | CH₃ | —(CH₂)₂—PO(OC₄H₉—n)₂ | H | 1 | CH | |
| 4.23 | OCH₃ | OCH₃ | —(CH₂)₂—PO(OC₄H₉—n)₂ | H | 1 | CH | |
| 4.24 | CH₃ | OCH₃ | —(CH₂)₂—PO(OC₄H₉—n)₂ | H | 1 | N | |
| 4.25 | OCH₃ | OCH₃ | —(CH₂)₂—PO(OC₄H₉—n)₂ | H | 1 | N | |
| 4.26 | CH₃ | OCH₃ | —(CH₂)₃—PO(OC₂H₅)₂ | H | 1 | CH | |
| 4.27 | OCH₃ | OCH₃ | —(CH₂)₃—PO(OC₂H₅)₂ | H | 1 | CH | |
| 4.28 | CH₃ | CH₃ | —(CH₂)₃—PO(OC₂H₅)₂ | H | 1 | CH | |
| 4.29 | CH₃ | OCH₃ | —(CH₂)₃—PO(OC₂H₅)₂ | H | 1 | N | |
| 4.30 | OCH₃ | OCH₃ | —(CH₂)₃—PO(OC₂H₅)₂ | H | 1 | N | |
| 4.31 | OCH₃ | OCH₃ | —PO(OC₂H₅)₂ | H | 1 | CH | m.p. 172° C. (decomp.) |
| 4.32 | OCH₃ | OCH₃ | —PO(OC₂H₅)₂ | H | 1 | CH | m.p. 172° C. (decomp.) |
| 4.33 | CH₃ | OCH₃ | —PO(OC₂H₅)₂ | H | 1 | CH | |

TABLE 4-continued

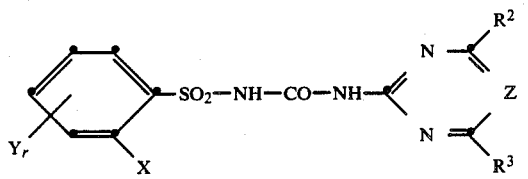

| No. | R² | R³ | X | Y | r | Z | Physical data |
|---|---|---|---|---|---|---|---|
| 4.34 | CH₃ | CH₃ | —PO(OC₂H₅)₂ | H | 1 | CH | |
| 4.35 | CH₃ | OCH₃ | —PO(OC₂H₅)₂ | H | 1 | N | |
| 4.36 | OCH₃ | OCH₃ | —PO(OC₂H₅)₂ | H | 1 | N | |
| 4.37 | OCH₃ | OCH₃ | —PO(CH₃)₂ | H | 1 | CH | |
| 4.38 | CH₃ | OCH₃ | —PO(CH₃)₂ | H | 1 | CH | |
| 4.39 | OCH₃ | OCH₃ | —PO(CH₃)₂ | H | 1 | CH | |
| 4.40 | CH₃ | OCH₃ | —PO(CH₃)₂ | H | 1 | N | |
| 4.41 | OCH₃ | OCH₃ | —PO(CH₃)₂ | H | 1 | N | |
| 4.42 | CH₃ | OCH₃ | —CH₂—PO(OC₂H₅)₂ | H | 1 | N | m.p. 120–125° C. (decomp.) |
| 4.43 | CH₃ | OCHF₂ | —NHCH₂—PO(OC₃H₇—i)₂ | H | 1 | CH | m.p. 109–111° C. (decomp.) |
| 4.44 | CH₃ | OCH₃ | —NHCH₂—PO(OC₃H₇—i)₂ | H | 1 | CH | m.p. 130–135° C. (decomp.) |
| 4.45 | CH₃ | OCH₃ | —CH₂—S—PS(OC₂H₅)₂ | H | 1 | N | m.p. 125–127° C. |
| 4.46 | CH₃ | OCH₃ | —CH₂—S—PS(OC₂H₅)₂ | H | 1 | CH | m.p. 145–147° C. |

FORMULATION EXAMPLES

EXAMPLE 11

Examples of formulations of active substances of the formula I (%=percent by weight)

| (a) Wettable powders | (a) | (b) | (c) |
|---|---|---|---|
| Active substance | 20% | 60% | 0.5% |
| Na Lignin sulfonate | 5% | 5% | 5% |
| Na Laurylsulfate | 3% | — | — |
| Na Diisobutylnaphthalenesulfonate | — | 6% | 6% |
| Octylphenol polyethylene glycol ether (7–8 moles of EO) | — | 2% | 2% |
| Highly disperse silica | 5% | 27% | 27% |
| Kaolin | 67% | | |
| Sodium chloride | — | — | 59.5% |

The active compound is thoroughly mixed with the adjuvants and the mixture is thoroughly ground in a suitable mill. This gives wettable powders which can be diluted with water to give suspensions of any desired concentration.

| (b) Emulsion concentrate | (a) | (b) |
|---|---|---|
| Active substance | 10% | 1% |
| Octylphenol polyethylene glycol ether (4–5 moles of EO) | 3% | 3% |
| Ca Dodecylbenzenesulfonate | 3% | 3% |
| Castor oil polyglycol ether (36 moles of EO) | 4% | 4% |
| Cyclohexanone | 30% | 10% |
| Mixed xylenes | 50% | 79% |

Emulsions of any desired concentration can be prepared from this concentrate by dilution.

| (c) Dusts | (a) | (b) |
|---|---|---|
| Active substance | 0.1% | 1% |
| Talc | 99.9% | — |
| Kaolin | — | 99% |

Ready-to-use dusts are obtained by mixing the active substance with carrier and grinding the mixture on a suitable mill.

| (d) Extruder granules | (a) | (b) |
|---|---|---|
| Active substance | 10% | 1% |
| Na Ligninsulfonate | 2% | 2% |
| Carboxymethylcellulose | 1% | 1% |
| Kaolin | 87% | 96% |

The active substance is mixed with the adjuvants, and the mixture is ground and moistened with water. This mixture is extruded and then dried in a stream of air.

| (e) Coated granules | |
|---|---|
| Active substance | 3% |
| Polyethylene glycol (MW 200) | 3% |
| Kaolin | 94% |

The active substance is finely ground and applied uniformly, in a mixer, to the kaolin, which has been moistened with polyethylene glycol. Dust-free coated granules are obtained in this manner.

| (f) Suspension concentrate | (a) | (b) |
|---|---|---|
| Active substance | 40% | 5% |
| Ethylene glycol | 10% | 10% |
| Nonylphenol polyethylene glycol ether (15 moles of EO) | 6% | 1% |
| Na Ligninsulfonate | 10% | 5% |
| Carboxymethylcellulose | 1% | 1% |
| 37% Aqueous formaldehyde solution | 0.2% | 0.2% |
| Silicon oil in the form of a 75% aqueous emulsion | 0.8% | 0.8% |
| Water | 32% | 77% |

The active substance is finely ground and intimately mixed with the adjuvants. This gives a suspension concentrate from which suspensions of any desired concentration can be prepared by dilution with water.

| (g) Salt solution | |
|---|---|
| Active substance | 5% |
| Isopropylamine | 1% |
| Octylphenol polyethylene glycol ether (78 moles of EO) | 3% |
| Water | 91% |

EXAMPLE 12

Herbicidal action before the emergence of the plants

Plastic pots are filled with expanded vermiculite (density: 0.135 g/cm$^3$; water absorption capacity: 0.565 l/l). After the vermiculite, which is not adsorptive, has been saturated with an aqueous emulsion of active substance in demineralised water, containing the active substances in a concentration of 70.8 ppm, seeds of the following plants are sown on the surface: Nasturtium officinalis, Agrostis tenuis, Stellaria media and Digitaria sanguinalis. The test vessels are then kept in an air-conditioned chamber at 20° C., an illumination of approx. 20 kLux and a relative humidity of 70%. During the germination phase of 4 to 5 days, the pots are covered with a translucent material and watered with demineralised water in order to increase the local humidity. After the 5th day, 0.5% of a commercial liquid fertiliser (®Greenzit) is added to the plant water. The test is evaluated 12 days after sowing, and the action on the test plants is assessed in accordance with the following scale:

1: plants have not germinated or are totally withered
2-3: very strong action
4-6: medium action
7-8: slight action
9: no action (like untreated control).

Pre-emergence action:

| Concentration of active substance emulsion: 70.8 ppm | | | | |
|---|---|---|---|---|
| Active substance No. | Test plant | | | |
| | Nasturtium | Stellaria | Agrostis | Digitaria |
| 4.6 | 3 | 6 | 3 | 8 |
| 4.31 | 2 | 1 | 1 | 3 |
| 4.45 | 2 | 2 | 2 | 2 |
| 4.46 | 2 | 2 | 1 | 2 |

EXAMPLE 13

Herbicidal action after the emergence of the plants (contact action)

After emergence, a number of weeds and crop plants, both monocotyledons and dicotyledons, were sprayed in the 4-leaf to 6-leaf stage with an aqueous dispersion of active substance containing 4 kg of active substance per hectare and were then kept at 24° to 26° C. and 45–60% relative humidity. The test is evaluated 15 days after the treatment and is assessed in accordance with the same scale as in the pre-emergence test.

Post-emergence action

| Application rate: 4 kg of active substance/hectare | | | | | | | |
|---|---|---|---|---|---|---|---|
| Compound No. | Avena | Setaria | Lolium | Solanum | Sinapis | Stellaria | Phaseolus |
| 4.31 | 9 | 6 | 5 | 7 | 2 | 3 | 5 |

EXAMPLE 14

Inhibition of growth in tropical soil-covering Leguminosae (cover crops)

The test plants (Centrosema plumieri and Centrosema pubescens) are cultivated until they have reached the fully grown stage, and are cut back to a height of 60 cm. After 7 days, the active substance is sprayed on in the form of an aqueous emulsion. The test plants are kept at 70% relative humidity and 6,000 Lux artificial light, for 14 hours per day at day temperatures of 27° and night temperatures of 21° C. The test is evaluated 4 weeks after application; this is effected by estimating and weighing the new growth in comparison with the control and by assessing the phytotoxicity. In this test, the plants treated with the active substances of the formula I show a marked reduction in new growth (less than 20% of the new growth in untreated control plants), without the test plants being damaged thereby.

EXAMPLE 15

Regulation of the growth of soya beans

Soya beans of the variety "Hark" are sown in a 6:3:1 soil-peat-sand mixture in plastic containers, and are put into an air-conditioned chamber. As a result of an optimum choice of temperature, illumination, addition of fertiliser and watering, the plants develop to the 5-leaf to 6-leaf trefoil stage after approx. 5 weeks. At this point in time, the plants are sprayed until they are thoroughly wetted with an aqueous liquor of an active substance of the formula I. The concentration of active substance is up to 100 g of active substance per hectare. Evaluation is carried out approx. 5 weeks after the application of the active substance. In comparison with untreated control plants, the active substances, according to the invention, of the formula I cause a noticeable increase in the number and weight of pods on the main shoot.

EXAMPLE 16

Inhibition of growth in cereals

The cereal species Hordeum vulgare (spring barley) and Secale (spring rye) are sown in a greenhouse in plastic pots containing sterilised soil, and are watered as required. Approx. 21 days after sowing, the shoots are sprayed with an aqueous spray liquor of an active substance of the formula I. The amount of active substance is up to 100 g of active substance per hectare. The growth of the cereal is assessed 21 days after application. In comparison with the untreated control, the treated plants show a decrease in new growth (60–90% of the control), and also, in some cases, an increase in the diameter of the stalk.

Example 17

Inhibition of growth in grasses

The grasses Lolium perenne, Poa pratensis, Festuca ovina, Dactylis glomerata and Cynodon dactylon are sown in a greenhouse in plastic trays containing a 6:3:1 soil-peat-sand mixture, and are watered as required. The emergent grasses are cut back every week to a height of 4 cm, and, approx. 50 days after sowing and 1 day after the last cutting, are sprayed with an aqueous spray liquor of an active substance of the formula I. The amount of active substance is equivalent to up to 100 g of active substance per hectare. The growth of the grasses is assessed 21 days after application.

What is claimed is:

1. A phenylsulfonamide of the formula

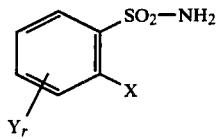

in which X is a group

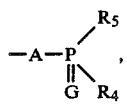

Y is hydrogen, halogen, $C_1$-$C_5$-alkyl, trifluoromethyl, $C_2$-$C_5$-alkenyl, $C_2$-$C_5$-alkynyl, nitro, —COOR$^6$ or —Q—R$^6$, A is a direct bond, $C_1$-$C_3$-alkylene or $C_2$-$C_3$-alkenylene, G is oxygen, R$^4$ is $C_1$-$C_5$-alkoxy, $C_1$-$C_5$-halogenoalkoxy, $C_1$-$C_5$-alkylthio, $C_1$-$C_5$-alkyl, $C_1$-$C_5$-halogenoalkyl, phenyl or hydroxyl, R$^5$ is hydrogen, $C_1$-$C_5$-alkoxy, $C_1$-$C_5$-halogenoalkoxy, $C_1$-$C_5$-alkylthio, $C_1$-$C_5$-alkyl or hydroxyl, R$^6$ is hydrogen, $C_1$-$C_5$-alkyl, $C_1$-$C_5$-halogenoalkyl or $C_2$-$C_6$-alkoxyalkyl Q is oxygen, sulfur, —SO— or —SO$_2$—.

2. A compound of claim 1, wherein Y is hydrogen.

3. A compound of claim 1, wherein Y is hydrogen, halogen, trifluoromethyl, nitro, amino or —COOR$^6$, R$^4$ is $C_1$-$C_4$-alkoxy, $C_1$-$C_2$-alkyl, phenyl or hydroxyl, R$^5$ is $C_1$-$C_4$-alkoxy, $C_1$-$C_2$-alkyl or hydroxyl and R$^6$ is hydrogen or lower alkyl.

4. The compound 2-diethoxyphosphonylbenzenesulfonamide of claim 1.

5. The compound 2-di-n-butoxyphosphonylvinylbenzenesulfonamide of claim 1.

* * * * *